US012686756B2

(12) United States Patent
Bodoc et al.

(10) Patent No.: US 12,686,756 B2
(45) **Date of Patent: *Jul. 21, 2026**

(54) INVERSE LATEX FOR A COSMETIC COMPOSITION COMPRISING A SPECIFIC SEQUESTERING AGENT AND A POLYELECTROLYTE COMBINING A STRONG ACID FUNCTION AND A WEAK ACID FUNCTION

(71) Applicant: SOCIÉTÉ D'EXPLOITATION DE PRODUITS POUR LES INDUSTRIES CHIMIQUES SEPPIC, Paris Cedex (FR)

(72) Inventors: Miruna Bodoc, Castres (FR); Aurelie Colas, La Garenne Colombes (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 954 days.

This patent is subject to a terminal disclaimer.

(21) Appl. No.: 17/783,200

(22) PCT Filed: Dec. 7, 2020

(86) PCT No.: PCT/EP2020/084857

§ 371 (c)(1),
(2) Date: Jun. 7, 2022

(87) PCT Pub. No.: WO2021/116009

PCT Pub. Date: Jun. 17, 2021

(65) Prior Publication Data

US 2023/0002590 A1 Jan. 5, 2023

(30) Foreign Application Priority Data

Dec. 9, 2019 (FR) ...................................... 1913965

(51) Int. Cl.

| | |
|---|---|
| ***C08K 5/17*** | (2006.01) |
| ***A61K 8/06*** | (2006.01) |
| ***A61K 8/44*** | (2006.01) |
| ***A61K 8/81*** | (2006.01) |
| ***A61K 9/00*** | (2006.01) |
| ***A61K 9/10*** | (2006.01) |
| ***A61K 47/32*** | (2006.01) |
| ***A61K 47/34*** | (2017.01) |
| ***A61Q 1/02*** | (2006.01) |
| ***A61Q 1/14*** | (2006.01) |
| ***A61Q 17/04*** | (2006.01) |
| ***A61Q 19/00*** | (2006.01) |
| ***C08F 220/06*** | (2006.01) |
| ***C08F 220/58*** | (2006.01) |
| ***C08F 222/38*** | (2006.01) |
| ***C08L 33/24*** | (2006.01) |

(52) U.S. Cl.

CPC .............. *C08K 5/175* (2013.01); *A61K 8/062* (2013.01); *A61K 8/44* (2013.01); *A61K 8/8158* (2013.01); *A61Q 1/02* (2013.01); *A61Q 1/14* (2013.01); *A61Q 17/04* (2013.01); *A61Q 19/00* (2013.01); *A61Q 19/007* (2013.01); *C08F 220/585* (2020.02); *A61K 2800/10* (2013.01); *A61K 2800/48* (2013.01); *A61K 2800/52* (2013.01)

(58) Field of Classification Search

None

See application file for complete search history.

(56) References Cited

U.S. PATENT DOCUMENTS 6,197,287 B1 * 3/2001 Mallo .................... A61Q 19/00 514/939
2010/0068643 A1 3/2010 Iwazaki et al.

(Continued)

FOREIGN PATENT DOCUMENTS

CN 104394843 A 3/2015
CN 107249557 A 10/2017
CN 107530271 A 1/2018

(Continued)

OTHER PUBLICATIONS

Innospec, "Biodegradable Chelant, Natrlquest E30," datasheet, Issue No. Jan. 2011, p. 1-4. (hereinafter Innospec). (Year: 2011).*

(Continued)

*Primary Examiner* — Ha S Nguyen
(74) *Attorney, Agent, or Firm* — NIXON & VANDERHYE

(57) ABSTRACT

Disclosed is a self-invertible inverse latex comprising an aqueous phase containing: a) a crosslinked anionic polyelectrolyte (P) including:—at least one first monomer unit derived from 2-methyl-2-[(1-oxo-2-propenyl) amino] 1-propanesulfonic acid in the form of a free or partially or totally salified acid;—at least one second monomer unit derived from at least one monomer selected from the elements of the group consisting of acrylic acid, methacrylic acid, 2-carboxyethyl acrylic acid, itaconic acid, maleic acid, 3-methyl 3-[(1-oxo-2-propenyl) amino] butanoic acid, the carboxylic function of said monomers being in the free, partially salified or totally salified acid form; and—at least one third monomer unit derived from a polyethylenic crosslinking monomer (AR); b) ethylenediamine disuccinic acid in the form of trisodium salt.

19 Claims, No Drawings

(56) References Cited

U.S. PATENT DOCUMENTS

| | | | | |
|---|---|---|---|---|
| 2011/0076245 | A1* | 3/2011 | Braun | A61K 8/33 424/59 |
| 2021/0007962 | A1 | 1/2021 | Bodoc et al. | |

FOREIGN PATENT DOCUMENTS

| | | | | |
|---|---|---|---|---|
| EP | 3 037 082 | | 6/2016 | |
| EP | 3037082 | A1 * | 6/2016 | A61K 8/8152 |
| FR | 2 794 124 | | 12/2000 | |
| JP | 2007146078 | A | 6/2007 | |
| JP | 2009144170 | A | 7/2009 | |
| JP | 2010072209 | A | 4/2010 | |
| JP | 2018048097 | A | 3/2018 | |
| WO | 96/00719 | | 1/1996 | |
| WO | 98/44902 | | 10/1998 | |
| WO | 03/103616 | | 12/2003 | |
| WO | 2019/170979 | | 9/2019 | |

OTHER PUBLICATIONS

Office Action issued in Chinese Patent Application No. 202080090530.3 dated Apr. 15, 2023.

International Search Report dated Feb. 15, 2021, for PCT/EP2020/084857, 5 pp. including English translation.

Written Opinion dated Feb. 15, 2021, for PCT/EP2020/084857, 7 pp.

Office Action, issued in Japanese Patent Application No. 2022-532796 dated Nov. 12, 2024.

* cited by examiner

INVERSE LATEX FOR A COSMETIC COMPOSITION COMPRISING A SPECIFIC SEQUESTERING AGENT AND A POLYELECTROLYTE COMBINING A STRONG ACID FUNCTION AND A WEAK ACID FUNCTION

This application is the U.S. national phase of International Application No. PCT/EP2020/084857 filed Dec. 7, 2020, which designated the U.S. and claims priority to FR 1913965 filed Dec. 9, 2019, the entire contents of each of which are hereby incorporated by reference.

BACKGROUND OF THE INVENTION

Field of the Invention

The present invention relates to a self-invertible inverse latex comprising a novel sequestering agent, to the process for preparing such a self-invertible inverse latex, to the use of said self-invertible inverse latexes as thickeners and/or emulsifiers and/or stabilizers used for preparing cosmetic or pharmaceutical compositions for topical use, and also to said compositions thus prepared.

Description of the Related Art

Polymers are widely used today in cosmetic formulations for topical use and represent the second most widely used family of products in formulations of this type. Cosmetic compositions contain polar phases, for instance phases consisting of water, and in most cases require the use of rheology-modifying polymers to increase the viscosity of these polar phases, and also to confer well-defined rheological behavior.

Among the polymers which modify the rheology of polar phases, mention may be made of natural polymers or synthetic polymers, and notably polymers of linear or branched, crosslinked or noncrosslinked, anionic or cationic, or amphiphilic, polyelectrolyte type. These polymers, once introduced into polar phases, have the property of spreading out under the effect of electrostatic repulsions due to the presence of the (negative and/or positive) charges on the linear or branched, noncrosslinked or crosslinked polymer backbone. Rheology-modifying agents provide both an increase in the viscosity of the polar phase, and also a degree of consistency and/or a stabilizing effect conferred on the cosmetic, dermocosmetic or demopharmaceutical formulation to be thickened.

In order to meet consumer needs and to improve cosmetic formulations for topical use, scientists have developed new innovative and varied polymer systems. Thus, the polymers used in cosmetics for topical use or dermocosmetics can act as film-forming agents, rheology modifiers, enable the stabilization of the fatty phases in the emulsions (of water-in-oil or oil-in-water type) or the stabilization of particles (pigments or fillers), or else confer specific sensory properties after application to the skin (for instance a soft feel, ease of handling and application, freshness effect, and the like), also having a direct impact on the appearance of the formula (translucent or opaque).

Rheology-modifying polymers for aqueous phases, mainly polyelectrolytes, result from the radical polymerization of (meth)acrylate type monomers, i.e. esters derived from acrylic acid or methacrylic acid, or else derivatives of acrylamide.

Today, these polymers, which can be provided in the form of an inverse latex, a concentrated inverse latex or a powder, make it possible to meet the needs of customers in terms of thickening performance, in a polar solvent, for instance water. The aqueous gels obtained once these polymers are dispersed in water have a smooth appearance, free from grains or lumps, with specific sensory properties to the touch, and also ease of handling and of application.

The liquid form, known under the name "self-invertible inverse latex", or its concentrated liquid form, is a composition which is provided in the form of a water-in-oil emulsion and comprises:

- an aqueous phase, itself comprising at least one polymer of polyelectrolyte type, of anionic, or cationic, or ampholytic type, which is linear and/or branched and/or crosslinked,
- a fatty phase comprising at least one oil,
- at least one emulsifying surfactant (S1) of water-in-oil type,
- at least one emulsifying surfactant (S2) of oil-in-water type,
- said polymer being obtained by performing an inverse emulsion radical polymerization process.

Radical polymerization is known for its sensitivity to the presence of impurities, even in small amounts. Compounds which may lead to a decrease in the rate of polymerization at low concentration are known as inhibitors or retarders. However, the distinction between these two effects is not always simple, and the same compound can have both harmful contributions depending on its concentration in the medium or on the nature of the monomers and of the reaction medium. Reproducible performance of the polymers which thicken an aqueous phase must be guaranteed in order to ensure a consistent quality of the cosmetic formulations for topical use containing these polymers. For this, industrial manufacturers must ensure that the polymerization reactions repeatably follow the same kinetics, more particularly regarding the inhibition time, the temperature increase profile, and the total duration of the polymerization reaction over time. Given these constraints, particular attention is given to the factors which can influence the start of the radical polymerization reaction, for example the presence of oxygen, which can retard the polymerization reaction by reacting with the radicals generated. These new peroxide radicals have a lower reactivity, since the initiation capacity is reduced. This is reflected by a weaker initiation step and a lower propagation rate, thus ultimately leading to polymers having different thickening properties. A step of deoxygenation of the medium, notably by purging with nitrogen before starting the polymerization reaction, thus proves necessary. Another factor directly impacting the polymerization is the presence of metallic species ($Fe2+$, $Fe3+$, $Cu2+$, and the like) which, in turn, generate an inhibitory effect. In this case, the inhibition can take place during the initiation phase by the reaction of the initiator radicals with metallic impurities, so that the active radical center then becomes incapable of fixing another monomer unit and becomes inactive during the polymerization.

The abovementioned metal ions can potentially originate from the starting materials or else from the items of equipment.

The monomers used for the preparation of self-invertible inverse latexes may have traces of metal cations. In the same way, it is not impossible to envisage the presence of metallic contaminants in the items of industrial equipment receiving the polymerization reactions. In most cases, the items of equipment are made of stainless steel and several types of stainless steel are encountered which differ in their composition. Stainless steel is an iron-based alloy, to which nickel, chromium or molybdenum are added in certain cases. It is chromium which gives stainless steel its antioxidant properties since, in the presence of oxygen, it is capable, by itself, of regenerating its surface chromium oxide layer, referred to as the passive layer. However, it is not impossible that, on prolonged contact with sources of pollution, acids, moisture, sea spray or iron-laden dust, or in the case of deep scratches, the protective layer will then become depassivated (therefore activated) and the stainless steel will become oxidized more quickly than it will be capable of protecting itself. In these cases, the appearance of rust may be found, which rust is thus a source of iron-based metal contaminants.

In view of the risks associated with the presence of all these sources of metal contaminants, the use of a sequestering agent is inescapable. The product generally used is the pentasodium salt of diethylenetriaminepentaacetic acid (also known under the brand name Versenex™ 80).

However, the change in the European regulations regarding the classification of the pentasodium salt of diethylenetriaminepentaacetic acid has led to the search for an alternative solution as sequestering agent for the preparation of self-invertible inverse latexes.

Starting therefrom, a problem which arises is that of providing a novel inverse latex with a novel sequestering agent which is as effective as the pentasodium salt of diethylenetriaminepentaacetic acid but which has properties more in conformity with the change in regulations.

SUMMARY OF THE INVENTION

One solution of the present invention is a self-invertible inverse latex comprising an aqueous phase comprising:

a) a crosslinked anionic polyelectrolyte (P) consisting of:
- at least one first monomer unit resulting from 2-methyl-2-[(1-oxo-2-propenyl)amino]-1-propanesulfonic acid in free acid form or partially or totally salified form;
- at least one second monomer unit derived from at least one monomer chosen from the elements of the group consisting of acrylic acid, methacrylic acid, 2-carboxyethylacrylic acid, itaconic acid, maleic acid, 3-methyl-3-[(1-oxo-2-propenyl)amino]butanoic acid, the carboxylic function of said monomers being in free acid form or partially salified or totally salified form;
- at least one third monomer unit derived from a polyethylenic crosslinking monomer (AR), b) ethylenediaminedisuccinic acid in trisodium salt form.

Depending on the case, the self-invertible inverse latex according to the invention may have one or more of the following features:
- the aqueous phase comprises at least 0.01 mol % of ethylenediaminedisuccinic acid in trisodium salt form;
- the polyethylenic crosslinking monomer (AR) is chosen from methylenebis(acrylamide), ethylene glycol dimethacrylate, diethylene glycol diacrylate, ethylene glycol diacrylate, diallylurea, triallylamine, trimethylolpropane triacrylate, diallyloxyacetic acid or a salt thereof, such as sodium diallyloxyacetate, or a mixture of these compounds;
- the crosslinking monomer (AR) is methylenebis(acrylamide) or triallylamine;
- the crosslinked anionic polyelectrolyte comprises, per 100 mol %: a proportion of between 20 mol % and 90 mol %, more particularly between 32 mol % and 90 mol %, and even more particularly between 40 mol % and 80 mol % of the monomer unit derived from 2-methyl-2-[(1-oxo-2-propenyl)amino]-1-propanesulfonic acid in free acid form or partially or totally salified form; a proportion of between 10 mol % and 80 mol %, more particularly between 10 mol % and 68 mol %, and even more particularly between 20 mol % and 60 mol % of the monomer unit derived from at least one monomer chosen from the members of the group consisting of acrylic acid, methacrylic acid, 2-carboxyethylacrylic acid, itaconic acid, maleic acid, 3-methyl-3-[(1-oxo-2-propenyl)amino]butanoic acid, the carboxylic function of said monomers being in free acid form or partially salified or totally salified form; and a proportion greater than 0 mol % and less than or equal to 1 mol %, more particularly a molar proportion less than or equal to 0.5%, more particularly less than or equal to 0.25% and most particularly less than or equal to 0.1%, and more particularly greater than or equal to 0.005 mol %, of monomer units derived from at least one polyethylenic crosslinking monomer unit (AR).

For the purposes of the present invention, the term "crosslinked anionic polyelectrolyte (P)" denotes, for the polymer (P), a nonlinear polyelectrolyte which is provided in the form of a three-dimensional network which is insoluble in water but which can swell in water and which then results in a chemical gel being obtained.

For the purposes of the present invention, the term "salified" indicates that the acid function present in a monomer exists in an anionic form combined in salt form with a cation, notably alkali metal salts, such as sodium or potassium cations, or such as cations of nitrogenous bases, such as the ammonium salt, the lysine salt or the monoethanolamine salt ($HOCH_2—CH_2—NH_3^+$). They are preferably sodium or ammonium salts.

According to a specific aspect of the present invention, said self-invertible inverse latex as defined above comprises from 20% by mass to 90% by mass, and more particularly from 30% by mass to 90% by mass, more particularly from 30% by mass to 80% by mass, and even more particularly from 33% by mass to 80% by mass, of said crosslinked anionic polyelectrolyte (P).

According to another particular aspect of the present invention, the molar proportion of monomer units derived from 2-methyl-2-[(1-oxo-2-propenyl)amino]-1-propanesulfonic acid in free acid or partially or totally salified form present in said crosslinked anionic polyelectrolyte (P) is greater than or equal to 32 mol % and less than or equal to 100 mol %, more particularly greater than or equal to 40 mol % and less than or equal to 100 mol %. According to another particular aspect of the present invention, the crosslinked anionic polyelectrolyte comprises, per 100 mol %: a proportion of between 20 mol % and 90 mol %, more particularly between 32 mol % and 90 mol %, and even more particularly between 40 mol % and 80 mol % of the monomer unit derived from 2-methyl-2-[(1-oxo-2-propenyl)amino]-1-propanesulfonic acid in free acid form or partially or totally salified form;

a proportion of between 10 mol % and 80 mol %, more particularly between 10 mol % and 68 mol %, and even more particularly between 20 mol % and 60 mol % of the monomer unit derived from at least one monomer chosen from the elements of the group consisting of acrylic acid, methacrylic acid, 2-carboxyethylacrylic acid, itaconic acid, maleic acid, 3-methyl-3-[(1-oxo-2-propenyl)amino]butanoic acid, the carboxylic function of said monomers being in free acid form or partially salified or totally salified form; and a proportion greater than 0 mol % and less than or equal to 1 mol %, more particularly a molar proportion less than or equal to 0.5%, more particularly less than or equal to 0.25% and most particularly less than or equal to 0.1%, and more particularly greater than or equal to 0.005 mol % of monomer units derived from at least one polyethylenic crosslinking monomer (AR). According to a particular aspect of the present invention, 2-methyl-2-[(1-oxo-2-propenyl)amino]-1-propanesulfonic acid is in the form of the sodium or ammonium salt.

According to a particular aspect of the present invention, the acrylic acid is in the sodium or ammonium salt form.

A subject of the present invention is also a process for preparing an inverse latex as defined above, comprising the following steps:

a) preparation of the aqueous phase as defined previously, b) preparation of an organic phase comprising at least one oil (0) and an emulsifying surfactant system (S1) of water-in-oil type, c) mixing the aqueous phase and the organic phase prepared in steps a) and b) and emulsifying so as to form an emulsion, d) inertizing the emulsion with nitrogen, e) initiating the polymerization reaction by introduction, into the inertized emulsion, of a free-radical initiator, and f) introduction, into the reaction medium resulting from step e), of an emulsifying surfactant system (S2) of oil-in-water type at a temperature of between 30° C. and 60° C.

Depending on the case, the process according to the invention may have one or more of the features below:

the process comprises between steps a) and b) a step of adding, to the aqueous phase prepared in step a), a solution chosen from a sodium hydroxide solution, a potassium hydroxide solution, an ammonium hydroxide solution, a monoethanolamine salt solution and a lysine salt solution;

in step e), the radical initiator is a redox pair which generates hydrogen sulfite ($HSO_3^-$) ions, such as the cumene hydroperoxide/sodium metabisulfite ($Na_2S_2O_5$) pair or the cumene hydroperoxide/thionyl chloride ($SOCl_2$) pair;

in step e), a polymerization coinitiator, preferably azobis (isobutyronitrile), is introduced into the inertized emulsion;

in step a), the pH of the aqueous phase is adjusted to between 3.0 and 7.0, more particularly between 3.5 and 6.5, even more particularly between 4.0 and 6.5;

the reaction medium resulting from step e) is concentrated by distillation before performing step f);

the reaction medium resulting from step e) or f) is spray-dried.

The term "oil (O)" notably denotes, in the definition of said self-invertible inverse latex:

linear alkanes including from 11 to 19 carbon atoms;

branched alkanes including from 7 to 40 carbon atoms, such as isododecane, isopentadecane, isohexadecane, isoheptadecane, isooctadecane, isononadecane or isoeicosane, or mixtures of some of them such as those mentioned below and identified by their INCI name: C7-8 isoparaffin, C8-9 isoparaffin, C9-11 isoparaffin, C9-12 isoparaffin, C9-13 isoparaffin, C9-14 isoparaffin, C9-16 isoparaffin, C10-11 isoparaffin, C10-12 isoparaffin, C10-13 isoparaffin, C11-12 isoparaffin, C11-13 isoparaffin, C11-14 isoparaffin, C12-14 isoparaffin, C12-20 isoparaffin, C13-14 isoparaffin, C13-16 isoparaffin;

cycloalkanes optionally substituted with one or more linear or branched alkyl radicals;

white mineral oils, such as the products sold under the following names: Marcol™ 52, Marcol™ 82, Drakeol™ 6VR, Eolane™ 130, Eolane™ 150;

hemisqualane (or 2,6,10-trimethyldodecane; CAS number: 3891-98-3), squalane (or 2,6,10,15,19,23-hexamethyltetracosane), hydrogenated polyisobutene or hydrogenated polydecene;

mixtures of alkanes including from 15 to 19 carbon atoms, said alkanes being linear alkanes, branched alkanes and cycloalkanes, and more particularly the mixture (M1) which comprises, per 100% of its mass, a mass proportion of branched alkanes of greater than or equal to 90% and less than or equal to 100%; a mass proportion of linear alkanes of greater than or equal to 0% and less than or equal to 9%, and more particularly less than 5%, and a mass proportion of cycloalkanes of greater than or equal to 0% and less than or equal to 1%, for example the mixtures sold under the name Emogreen™ L15 or Emogreen™ L19;

the fatty alcohol ethers of formula (IV):

$$Z1—O—Z2, \quad (IV)$$

in which Z1 and Z2, which may be identical or different, represent a linear or branched alkyl radical including from 5 to 18 carbon atoms, for example dioctyl ether, didecyl ether, didodecyl ether, dodecyl octyl ether, dihexadecyl ether, (1,3-dimethylbutyl) tetradecyl ether, (1,3-dimethylbutyl) hexadecyl ether, bis(1,3-dimethylbutyl) ether or dihexyl ether;

monoesters of fatty acids and of alcohols of formula (V):

$$R'1—(C{=}O)—O—R'2, \quad (V)$$

in which R'1-(C=O) represents a saturated or unsaturated, linear or branched acyl radical including from 8 to 24 carbon atoms, and R'2 represents, independently of R'1, a saturated or unsaturated, linear or branched hydrocarbon-based chain including from 1 to 24 carbon atoms, for example methyl laurate, ethyl laurate, propyl laurate, isopropyl laurate, butyl laurate, 2-butyl laurate, hexyl laurate, methyl cocoate, ethyl cocoate, propyl cocoate, isopropyl cocoate, butyl cocoate, 2-butyl cocoate, hexyl cocoate, methyl myristate, ethyl myristate, propyl myristate, isopropyl myristate, butyl myristate, 2-butyl myristate, hexyl myristate, octyl myristate, methyl palmitate, ethyl palmitate, propyl palmitate, isopropyl palmitate, butyl palmitate, 2-butyl palmitate, hexyl palmitate, octyl palmitate, methyl oleate, ethyl oleate, propyl oleate, isopropyl oleate, butyl oleate, 2-butyl oleate, hexyl oleate, octyl oleate, methyl stearate, ethyl stearate, propyl stearate, isopropyl stearate, butyl stearate, 2-butyl stearate, hexyl stearate, octyl stearate, methyl isostearate, ethyl isostearate, propyl isostearate, isopropyl isostearate, butyl isostearate, 2-butyl isostearate, hexyl isostearate, isostearyl isostearate;

diesters of fatty acids and of glycerol of formula (VI) and of formula (VII):

(VI)

R'3—(C=O)—O—CH2—CH(OH)—CH2—O—(C=O)—R'4, (VII)

R'5—(C=O)—O—CH2—CH[O—(C=O)—R'6]—CH2—OH, in which formulae (VI) and (VII) R'3-(C=O), R'4-(C=O), R'5-(C=O) and R'6-(C=O), which may be identical or different, represent a saturated or unsaturated, linear or branched acyl group including from 8 to 24 carbon atoms;

triesters of fatty acids and of glycerol of formula (VIII):

(VIII)

R'7—(C=O)—O—CH2—CH[O—(C=O)—R″8]—CH2—O—(C=O)—R″9, in which R'7-(C=O), R'8-(C=O) and R'9-(C=O), which may be identical or different, represent a saturated or unsaturated, linear or branched acyl group including from 8 to 24 carbon atoms. According to another particular aspect of the present invention, said oil (H) is chosen from undecane, tridecane, isododecane and isohexadecane, mixtures of alkanes and of isoalkanes and of cycloalkanes, for instance the mixture (M1) as defined previously and the mixtures sold under the names Emogreen™115, Emogreen®119, Emosmart™115, Emosmart™119, Emosmart™V21, Isopar™L or Isopar™M; the white mineral oils sold under the names Marcol™52, Marcol™82, Drakeol™6VR, Eolane™130 or Eolane™150; hemisqualane, squalane, hydrogenated polyisobutene or hydrogenated polydecene; dioctyl ether or didecyl ether; isopropyl myristate, hexyl palmitate, octyl palmitate, isostearyl isostearate, octanoyl/decanoyl triglyceride, hexadecanoyl/octadecanoyl triglyceride, triglycerides derived from rapeseed oil, from sunflower oil, from linseed oil or from palm oil.

In said self-invertible inverse latex that is the subject of the present invention, the emulsifying system (S1) of water-in-oil type consists either of a single emulsifying surfactant or of a mixture of emulsifying surfactants, on condition that said resulting emulsifying system (S1) has an HLB value that is low enough to lead to the formation of emulsions of water-in-oil type.

As emulsifying surfactant (S1) of water-in-oil type, examples include anhydrohexitol esters of linear or branched, saturated or unsaturated aliphatic carboxylic acids, including from 12 to 22 carbon atoms, optionally substituted with one or more hydroxyl groups, and more particularly esters of anhydrohexitols chosen from anhydrosorbitols and anhydromannitols and of linear or branched, saturated or unsaturated aliphatic carboxylic acids including from 12 to 22 carbon atoms, optionally substituted with one or more hydroxyl groups. According to another particular aspect of the present invention, said emulsifying system (S1) of water-in-oil type is chosen from the elements of the group consisting of sorbitan laurate, for example the product sold under the name Montane™ 20, sorbitan palmitate, for example the product sold under the name Montane™ 40, sorbitan stearate, for example the product sold under the name Montane™ 60, sorbitan oleate, for example the product sold under the name Montane™ 80, sorbitan sesquioleate, for example the product sold under the name Montane™ 85, sorbitan trioleate, for example the product sold under the name Montane™ 83, sorbitan isolaurate, sorbitan isostearate, for example the product sold under the name Montane™ 70, mannitan laurate, mannitan oleate, or a mixture of these esters; polyesters with a molecular weight of between 1000 and 3000 and derived from condensation between a poly(isobutenyl)succinic acid or the anhydride thereof, such as Hypermer™ 2296, or the mixture sold under the brand name Simaline™ IE 501A, the polyglycol polyhydroxystearates of formula (IX):

[Chem 1]

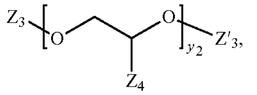

(IX)

in which formula (IX) y2 represents an integer greater than or equal to 2 and less than or equal to 50, Z4 represents a hydrogen atom, a methyl radical or an ethyl radical, and Z3 represents a radical of formula (X):

[Chem 2]

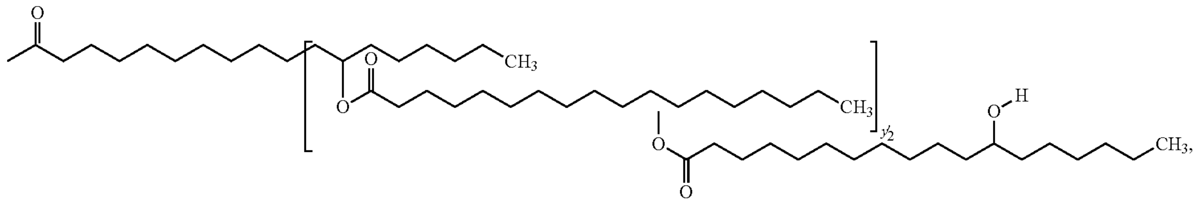

(X)

in which formula (X) y'2 represents an integer greater than or equal to 0 and less than or equal to 10, more particularly greater than or equal to 1 and less than or equal to 10 and Z'3 represents a radical of formula (X) as defined above, with Z3' being identical to or different from Z3, or a hydrogen atom.

Examples of emulsifying surfactants of water-in-oil type of formula (IX) that may be used to prepare the emulsifying system (S1) are PEG-30 dipolyhydroxystearate sold under the name Simaline™ WO, or mixtures comprising PEG-30 dipolyhydroxystearate and sold under the names Simaline™IE 201 A and Simaline™IE 201 B, or the mixture comprising trimethylolpropane-30 tripolyhydroxystearate sold under the name Simaline™IE 301 B. According to a particular aspect of the invention, the emulsifying system of oil-in-water type (S2) comprises, per 100% of its mass, a proportion of greater than or equal to 50% by mass and less than or equal to 100% of a composition (Ce) which comprises, per 100% of its mass: from 10% by mass to 60% by mass, more particularly from 15% by mass to 60% by mass and most particularly from 15% by mass to 50% by mass of at least one compound of formula (I):

$$HO—[CH2—CH(OH)—CH2—O]n—H \quad (I)$$

in which n represents an integer greater than or equal to 1 and less than or equal to 15; from 40% by mass to 90% by mass, more particularly from 40% by mass to 85% by mass and most particularly from 50% by mass to 85% by mass of at least one compound of formula (II):

$$R1—(C{=}O)—[O—CH2—CH(OH)—CH2]p—OH, \quad (II)$$

in which p, which is different from or identical to n, represents an integer greater than or equal to 1 and less than or equal to 15; and in which the group R1-(C═O)— represents a saturated or unsaturated, linear or branched aliphatic radical including from 6 to 22 carbon atoms; and optionally up to 30% by mass, more particularly from 0% by mass to 25% by mass and most particularly from 0% by mass to 20% by mass of at least one composition (C11) represented by formula (III):

$$HO—[CH2—CHOH—CH2—O—]q—(G)r—H, \quad (III)$$

in which q, which is different from or identical to n, represents an integer greater than or equal to 1 and less than or equal to 3, G represents a reducing sugar residue and r represents a decimal number greater than or equal to 1.05 and less than or equal to 5.00;

said composition (C11) consisting of a mixture of the compounds of formulae (III1), (III2), (III3), (III4) and (III5):

$$HO—[CH2—CHOH—CH2—O—]q—O—(G)1—H, \quad (III1)$$

$$HO—[CH2—CHOH—CH2—O—]q—O—(G)2—H, \quad (III2)$$

$$HO—[CH2—CHOH—CH2—O—]q—O—(G)3—H, \quad (III3)$$

$$HO—[CH2—CHOH—CH2—O—]q—O—(G)4—H, \quad (III4)$$

$$HO—[CH2—CHOH—CH2—O—]q—O—(G)5—H, \quad (III5)$$

in molar proportions of said compounds of formulae (III1), (III2), (III3), (III4) and (III5) respectively equal to a1, a2, a3, a4 and a5, such that the sum (a1+a2+a3+a4+a5) is equal to 1, and such that the sum (a1+2a2+3a3+4a4+5a5) is equal to r.

The emulsifying system (S2) of oil-in-water type consists either of the composition (Ce) alone or of a mixture of said composition (Ce) with one or more other emulsifying surfactants, provided that said resulting emulsifying system (S2) has a sufficiently high HLB value to bring about the formation of emulsions of oil-in-water type.

The term "reducing sugar" in formula (III) as defined previously denotes saccharide derivatives that do not have in their structures any glycoside bond established between an anomeric carbon and the oxygen of an acetal group as defined in the reference publication: "Biochemistry", Daniel Voet/Judith G. Voet, page 250, John Wiley & Sons, 1990. The oligomeric structure $(G)_x$ may be in any isomeric form, whether it is optical isomerism, geometrical isomerism or regioisomerism; it may also represent a mixture of isomers.

As regards the polymerization reaction, it is initiated in step e) at a preferential temperature of 10° C., then performed either quasi-adiabatically up to a temperature of greater than or equal to 50° C., or by controlling the temperature.

A subject of the invention is also the use of said self-invertible inverse latex as defined previously, as a thickener and/or emulsifier and/or stabilizer for a cosmetic or pharmaceutical topical composition.

A subject of the invention is also a topical cosmetic composition (F) or a topical pharmaceutical composition (G), characterized in that it comprises, as thickener, per 100% of its total mass, between 0.1% and 10% by mass of said self-invertible inverse latex as defined previously.

The term "topical" used in the definitions of said compositions (F) and (G) means that they are employed by application to the skin, the hair, the scalp or the mucous membranes, whether it concerns a direct application, in the case of a cosmetic, dermocosmetic, dermopharmaceutical or pharmaceutical preparation, or an indirect application, for example in the case of a bodycare product in the form of a textile or paper wipe or of sanitary products intended to be in contact with the skin or the mucous membranes.

Said compositions (F) and (G) are generally provided in the form of an aqueous or aqueous/alcoholic or aqueous/glycol solution, in the form of a suspension, of an emulsion, of a microemulsion or of a nanoemulsion, whether they are of water-in-oil, oil-in-water, water-in-oil-in-water or oil-in-water-in-oil type.

Said compositions (F) and (G) can be packaged in a bottle, in a device of "pump-action spray" type, in pressurized form in an aerosol device, in a device equipped with a perforated wall, such as a grate, or in a device equipped with a ball applicator (known as a "roll-on"). In general, said compositions (F) and (G) also include excipients and/or active principles usually used in the field of formulations for topical use, in particular cosmetic, dermocosmetic, pharmaceutical or dermopharmaceutical formulations, such as thickening and/or gelling surfactants, stabilizers, film-forming compounds, hydrotropic agents, plasticizers, emulsifying and coemulsifying agents, opacifiers, nacreous agents, superfatting agents, sequestering agents, chelating agents, antioxidants, fragrances, preserving agents, conditioning agents, whitening agents intended for bleaching bodily hairs and the skin, active principles intended to contribute a treating action with regard to the skin or hair, sunscreens, pigments or mineral fillers, particles providing a visual effect or intended for the encapsulation of active principles, exfoliating particles or texturing agents.

Examples of foaming and/or detergent surfactants that may be combined with said self-invertible inverse latex as defined previously in said compositions (F) and (G) include anionic, cationic, amphoteric or nonionic foaming and/or detergent surfactants.

The foaming and/or detergent anionic surfactants that may be combined with said self-invertible inverse latex as defined previously in said compositions (F) and (G) include alkali metals salts, alkaline-earth metal salts, ammonium salts, amine salts or amino alcohol salts of alkyl ether sulfates, of alkyl sulfates, of alkylamido ether sulfates, of alkylaryl polyether sulfates, of monoglyceride sulfates, of α-olefin sulfonates, of paraffin sulfonates, of alkyl phosphates, of alkyl ether phosphates, of alkyl sulfonates, of alkylamide sulfonates, of alkylaryl sulfonates, of alkyl carboxylates, of alkylsulfosuccinates, of alkyl ether sulfosuccinates, of alkylamide sulfosuccinates, of alkylsulfoacetates, of alkyl sarcosinates, of acylisethionates, of N-acyl taurates, of acyl lactylates, of N-acylamino acid derivatives, of N-acyl peptide derivatives, of N-acyl protein derivatives, of N-acyl fatty acid derivatives.

The foaming and/or detergent amphoteric surfactants that may be combined with said self-invertible inverse latex as defined previously in said compositions (F) and (G) include alkyl betaines, alkyl amido betaines, sultaines, alkyl amidoalkyl sulfobetaines, imidazoline derivatives, phosphobetaines, amphopolyacetates and amphopropionates.

The foaming and/or detergent cationic surfactants that may be combined with said self-invertible inverse latex as defined previously in said compositions (F) and (G) particularly include quaternary ammonium derivatives.

The foaming and/or detergent nonionic surfactants that may be combined with said self-invertible inverse latex as defined previously in said compositions (F) and (G) more particularly include alkyl polyglycosides including a linear or branched and saturated or unsaturated aliphatic radical including from 8 to 16 carbon atoms, such as octyl polyglucoside, decyl polyglucoside, undecylenyl polyglucoside, dodecyl polyglucoside, tetradecyl polyglucoside, hexadecyl polyglucoside or 1,12-dodecanediyl polyglucoside; ethoxylated hydrogenated castor oil derivatives, such as the product sold under the INCI name PEG-40 hydrogenated castor oil; polysorbates, such as Polysorbate 20, Polysorbate 40, Polysorbate 60, Polysorbate 70, Polysorbate 80 or Polysorbate 85; coconut kernel amides; or N-alkylamines.

Examples of thickening and/or gelling surfactants that may be combined with said self-invertible inverse latex as defined previously in said compositions (F) and (G) include optionally alkoxylated alkyl polyglycoside fatty esters, such as ethoxylated methyl polyglucoside esters, for example the PEG 120 methyl glucose trioleate and the PEG 120 methyl glucose dioleate sold respectively under the names Glucamate™ LT and Glucamate™ DOE-120; alkoxylated fatty esters, such as the PEG 150 pentaerythrityl tetrastearate sold under the name Crothix™ DS53 or the PEG 55 propylene glycol oleate sold under the name Antil™ 141; fatty-chain polyalkylene glycol carbamates, such as the PPG-14 laureth isophoryl dicarbamate sold under the name Elfacos™ T211 or the PPG-14 palmeth-60 hexyl dicarbamate sold under the name Elfacos™ GT2125.

Examples of thickening and/or gelling agents that may be combined with said self-invertible inverse latex as defined previously in said compositions (F) and (G) include copolymers of AMPS and of alkyl acrylates, the carbon chain of which comprises between 4 and 30 carbon atoms and more particularly between 10 and 30 carbon atoms, linear, branched or crosslinked terpolymers of at least one monomer bearing a free, partially salified or totally salified strong acid function with at least one neutral monomer and at least one monomer of formula (XIII):

(XIII)

$$CH2{=}C(R'3){-}C({=}O){-}[CH2{-}CH2{-}O[_{n'}{-}R'4$$

in which R'3 represents a hydrogen atom or a methyl radical, R'4 represents a linear or branched alkyl radical including from 8 to 30 carbon atoms and n' represents a number greater than or equal to 1 and less than or equal to 50.

Examples of thickening and/or gelling agents that may be combined with said self-invertible inverse latex as defined previously in said compositions (F) and (G) include polysaccharides consisting solely of monosaccharides, such as glucans or glucose homopolymers, glucomannoglucans, xyloglycans, galactomannans, the degree of substitution (DS) of the D-galactose units on the main D-mannose chain of which is between 0 and 1 and more particularly between 1 and 0.25, such as galactomannans originating from cassia gum (DS=1/5), locust bean gum (DS=1/4), tara gum (DS=1/3), guar gum (DS=1/2) or fenugreek gum (DS=1).

Examples of thickening and/or gelling agents that may be combined with said self-invertible inverse latex as defined previously in said compositions (F) and (G) include polysaccharides consisting of monosaccharide derivatives, such as sulfated galactans and more particularly carrageenans and agar, uronans and more particularly algins, alginates and pectins, heteropolymers of monosaccharides and of uronic acids and more particularly xanthan gum, gellan gum, gum arabic exudates and karaya gum exudates, or glucosaminoglycans.

Examples of thickening and/or gelling agents that may be combined with said self-invertible inverse latex as defined previously in said compositions (F) and (G) include cellulose, cellulose derivatives, such as methyl cellulose, ethyl cellulose or hydroxypropyl cellulose, silicates, starch, hydrophilic starch derivatives or polyurethanes.

Examples of stabilizers that may be combined with said self-invertible inverse latex as defined previously in said compositions (F) and (G) include monocrystalline waxes and more particularly ozokerite, mineral salts, such as sodium chloride or magnesium chloride, or silicone polymers, such as polysiloxane polyalkyl polyether copolymers.

Examples of solvents that may be combined with said self-invertible inverse latex as defined previously in said compositions (F) and (G) include water, organic solvents, such as glycerol, diglycerol, glycerol oligomers, ethylene glycol, propylene glycol, butylene glycol, 1,3-propanediol, 1,2-propanediol, hexylene glycol, diethylene glycol, xylitol, erythritol, sorbitol, water-soluble alcohols, such as ethanol, isopropanol or butanol, or mixtures of water and of said organic solvents.

Examples of thermal or mineral waters that may be combined with said self-invertible inverse latex as defined previously in said compositions (F) and (G) include thermal or mineral waters having a mineralization of at least 300 mg/l, in particular Avène water, Vittel water, Vichy basin water, Uriage water, La Roche-Posay water, La Bourboule water, Enghien-les-Bains water, Saint-Gervais-les-Bains water, Néris-les-Bains water, Allevard-les-Bains water, Digne water, Maizières water, Neyrac-les-Bains water, Lons-le-Saunier water, Rochefort water, Saint Christau water, Les Fumades water and Tercis-les-Bains water.

Examples of hydrotropic agents that may be combined with said self-invertible inverse latex as defined previously in said compositions (F) and (G) include xylenesulfonates, cumenesulfonates, hexyl polyglucoside, 2-ethylhexyl polyglucoside and n-heptyl polyglucoside.

Examples of emulsifying surfactants that may be combined with said self-invertible inverse latex as defined previously in said compositions (F) and (G) include nonionic surfactants, anionic surfactants or cationic surfactants.

Examples of emulsifying nonionic surfactants that may be combined with said self-invertible inverse latex as defined previously in said compositions (F) and (G) include esters of fatty acids and of sorbitol, such as the products sold under the names Montane™ 40, Montane™ 60, Montane™ 70, Montane™ 80 and Montane™ 85; compositions comprising glycerol stearate and stearic acid ethoxylated with between 5 mol and 150 mol of ethylene oxide, such as the composition comprising stearic acid ethoxylated with 135 mol of ethylene oxide and glycerol stearate sold under the name Simulsol™ 165; mannitan esters; ethoxylated mannitan esters; sucrose esters; methyl glucoside esters; alkyl polyglycosides including a linear or branched and saturated or unsaturated aliphatic radical and including from 14 to 36 carbon atoms, such as tetradecyl polyglucoside, hexyldecyl polyglucoside, octadecyl polyglucoside, hexyldecyl polyxyloside, octadecyl polyxyloside, eicosyl polyglucoside, dodecosyl polyglucoside, 2-octyldodecyl polyxyloside or 12-hydroxystearyl polyglucoside; compositions of linear or branched and saturated or unsaturated fatty alcohols and including from 14 to 36 carbon atoms and of alkyl polyglycosides such as described above, for example the compositions sold under the names Montanov™ 68, Montanov™ 14, Montanov™ 82, Montanov™ 202, Montanov™ S, Montanov™ W018, Montanov™ L, Fluidanov™ 20X and Easynov™.

Examples of anionic surfactants that may be combined with said self-invertible inverse latex as defined previously in said compositions (F) and (G) include glyceryl stearate citrate, cetearyl sulfate, soaps, such as sodium stearate or triethanolammonium stearate, and N-acylamino acid derivatives which are salified, for example stearoyl glutamate.

Examples of cationic emulsifying surfactants that may be combined with said self-invertible inverse latex as defined previously in said compositions (F) and (G) include amine oxides, quaternium-82 and the surfactants described in patent application WO 96/00719 and mainly those whose fatty chain comprises at least 16 carbon atoms.

Examples of opacifying and/or nacreous agents that may be combined with said self-invertible inverse latex as defined previously in said compositions (F) and (G) include sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate or fatty alcohols including from 12 to 22 carbon atoms.

Examples of texturing agents that may be combined with said self-invertible inverse latex as defined previously in said compositions (F) and (G) include N-acylamino acid derivatives, such as lauroyl lysine sold under the name Aminohope™ LL, starch octenylsuccinate sold under the name Dryflo™, myristyl polyglucoside sold under the name Montanov™ 14, cellulose fibers, cotton fibers, chitosan fibers, talc, sericite or mica.

Examples of deodorant agents that may be combined with said self-invertible inverse latex as defined previously in said compositions (F) and (G) include alkali metal silicates, zinc salts, such as zinc sulfate, zinc gluconate, zinc chloride or zinc lactate; quaternary ammonium salts, such as cetyltrimethylammonium salts or cetylpyridinium salts; glycerol derivatives, such as glycerol caprate, glycerol caprylate or polyglycerol caprate; 1,2-decanediol, 1,3-propanediol; salicylic acid; sodium bicarbonate; cyclodextrins; metallic zeolites; Triclosan™; aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum sulfate, sodium aluminum lactate, complexes of aluminum chlorohydrate and of glycol, such as the complex of aluminum chlorohydrate and of propylene glycol, the complex of aluminum dichlorohydrate and of propylene glycol, the complex of aluminum sesquichlorohydrate and of propylene glycol, the complex of aluminum chlorohydrate and of polyethylene glycol, the complex of aluminum dichlorohydrate and of polyethylene glycol, or the complex of aluminum sesquichlorohydrate and of polyethylene glycol.

Examples of oils that may be combined with said self-invertible inverse latex as defined previously in said compositions (F) and (G) include mineral oils, such as liquid paraffin, liquid petroleum jelly, isoparaffins or white mineral oils; oils of animal origin, such as squalene or squalane; plant oils, such as phytosqualane, sweet almond oil, coconut kernel oil, castor oil, jojoba oil, olive oil, rapeseed oil, groundnut oil, sunflower oil, wheat germ oil, corn germ oil, soybean oil, cottonseed oil, alfalfa oil, poppy oil, pumpkinseed oil, evening primrose oil, millet oil, barley oil, rye oil, safflower oil, candlenut oil, passionflower oil, hazelnut oil, palm oil, shea butter, apricot kernel oil, beauty-leaf oil, sisymbrium oil, avocado oil, calendula oil, oils resulting from flowers or vegetables, ethoxylated plant oils; synthetic oils, such as fatty acid esters, for example butyl myristate, propyl myristate, isopropyl myristate, cetyl myristate, isopropyl palmitate, octyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, fatty acid monoglycerides, diglycerides and triglycerides, such as glycerol triheptanoate, alkylbenzoates, hydrogenated oils, poly($\alpha$-olefins), polyolefins, such as poly(isobutene), synthetic isoalkanes, such as isohexadecane or isododecane, or perfluorinated oils; silicone oils, such as dimethylpolysiloxanes, methylphenylpolysiloxanes, silicones modified with amines, silicones modified with fatty acids, silicones modified with alcohols, silicones modified with alcohols and fatty acids, silicones modified with polyether groups, epoxy-modified silicones, silicones modified with fluoro groups, cyclic silicones and silicones modified with alkyl groups. In the present patent application, the term "oils" refers to compounds and/or mixtures of compounds which are water-insoluble, and which have a liquid appearance at a temperature of 25° C.

Examples of waxes that may be combined with said self-invertible inverse latex as defined previously in said compositions (F) and (G) include beeswax, carnauba wax, candelilla wax, ouricury wax, Japan wax, cork fiber wax, sugarcane wax, paraffin waxes, lignite waxes, microcrystalline waxes, lanolin wax; ozokerite, polyethylene wax, silicone waxes, plant waxes, fatty alcohols and fatty acids which are solid at room temperature, or glycerides which are solid at room temperature. In the present patent application, the term "waxes" refers to compounds and/or mixtures of compounds which are water-insoluble, and which have a solid appearance at a temperature of greater than or equal to 45° C.

As examples of active principles that may be combined with said self-invertible inverse latex as defined previously in said compositions (F) and (G), mention may be made of vitamins and their derivatives, notably their esters, such as retinol (vitamin A) and its esters (for example retinyl palmitate), ascorbic acid (vitamin C) and its esters, sugar derivatives of ascorbic acid (such as ascorbyl glucoside), tocopherol (vitamin E) and its esters (such as tocopheryl acetate), vitamin B3 or B10 (niacinamide and its derivatives); compounds showing a lightening or depigmenting action on the skin, such as w-undecylenoyl phenylalanine sold under the name Sepiwhite™ MSH, Sepicalm™ VG, the glycerol monoester and/or the glycerol diester of w-undecylenoyl phenylalanine, w-undecylenoyl dipeptides, arbutin, kojic acid, hydroquinone; compounds showing a calmative action, notably Sepicalm™ S, allantoin and bisabolol; anti-inflammatory agents; compounds showing a moisturizing action, such as urea, hydroxyureas, glycerol, polyglycerols, glycerol glucoside, diglycerol glucoside, polyglyceryl glucosides, xylityl glucoside; polyphenol-rich plant extracts, such as grape extracts, pine extracts, wine extracts or olive extracts; compounds showing a slimming or lipolytic action, such as caffeine or its derivatives, Adiposlim™, Adipoless™, fucoxanthin; N-acylated proteins; N-acylated peptides, such as Matrixyl™; N-acylated amino acids; partial hydrolyzates of N-acylated proteins; amino acids; peptides; total hydrolyzates of proteins; soybean extracts, for example Raffermine™; wheat extracts, for example Tensine™ or Gliadine™; plant extracts, such as tannin-rich plant extracts, isoflavone-rich plant extracts or terpene-rich plant extracts; extracts of freshwater or marine algae; marine plant extracts; marine extracts in general, such as corals; essential waxes; bacterial extracts; ceramides; phospholipids; compounds showing an antimicrobial action or a purifying action, such as Lipacide™ C8G, Lipacide™ UG, Sepicontrol™ A5, Octopirox™ or Sensiva™ SC50; compounds showing an energizing or stimulating property, such as Physiogenyl™, panthenol and its derivatives, such as Sepicap™ MP; anti-aging active principles, such as Sepilift™ DPHP, Lipacide™ PVB, Sepivinol™, Sepivital™, Manoliva™, Phyto-Age™, Timecode™; Survicode™; antiphotoaging active principles; active principles which protect the integrity of the dermoepidermal junction; active principles which increase the synthesis of the components of the extracellular matrix, such as collagen, elastins or glycosaminoglycans; active principles which act favorably on chemical cell communication, such as cytokines, or physical cell communication, such as integrins; active principles which create a sensation of "heating" on the skin, such as activators of cutaneous microcirculation (such as nicotinic acid derivatives) or products which create a sensation of "coolness" on the skin (such as menthol and derivatives); active principles which improve cutaneous microcirculation, for example venotonics; draining active principles; active principles having a decongestant purpose, such as *Ginkgo biloba*, ivy, horse chestnut, bamboo, Ruscus, butcher's broom, *Centella asiatica*, fucus, rosemary or willow extracts; agents for tanning or browning the skin, for example dihydroxyacetone (DHA), erythrulose, mesotartaric aldehyde, glutaraldehyde, glyceraldehyde, alloxan or ninhydrin, plant extracts, for example extracts of red woods of the genus *Pterocarpus* and of the genus *Baphia*, such as *Pteropcarpus santalinus, Pterocarpus osun, Pterocarpus soyauxii, Pterocarpus erinaceus, Pterocarpus indicus* or *Baphia nitida*, such as those described in the European patent application EP 0 971 683; agents known for their action in facilitating and/or accelerating tanning and/or browning of human skin, and/or for their action in coloring human skin, for example carotenoids (and more particularly β-carotene and γ-carotene), the product sold under the brand name Carrot Oil (INCI name: *Daucus carrota, Helianthus annuus* sunflower oil) by the company Provital, which contain carotenoids, vitamin E and vitamin K; tyrosine and/or its derivatives, known for their effect on the acceleration of the tanning of human skin in combination with exposure to ultraviolet radiation, for example the product sold under the brand name SunTan Accelerator™ by the company Provital, which contains tyrosine and riboflavins (vitamin B), the complex of tyrosine and of tyrosinase sold under the brand name Zymo Tan Complex by the company Zymo Line, the product sold under the brand name MelanoBronze™ (INCI name: Acetyl Tyrosine, Monk's pepper extract (*Vitex agnus-castus*)) by the company Mibelle, which contains acetyl tyrosine, the product sold under the brand name Unipertan VEG-24/242/2002 (INCI name: Butylene Glycol and Acetyl Tyrosine and Hydrolyzed Vegetable Protein and Adenosine Triphosphate) by the company Unipex, the product sold under the brand name Try-Excell™ (INCI name: Oleoyl tyrosine and *Luffa cylindrica* (seed) oil and oleic acid) by the company the company Sederma, which contains extracts of marrow seeds (or loofah oil), the product sold under the brand name Actibronze™ (INCI name: Hydrolyzed wheat protein and acetyl tyrosine and copper gluconate) by the company the company Alban Muller, the product sold under the brand name Tyrostan™ (INCI name: Potassium caproyl tyrosine) by the company the company Synerga, the product sold under the brand name Tyrosinol (INCI name: Sorbitan Isostearate, Glyceryl Oleate, Caproyl Tyrosine) by the company Synerga, the product sold under the brand name InstaBronze™ (INCI name: Dihydroxyacetone and Acetyl Tyrosine and Copper Gluconate) by the company Alban Muller, the product sold under the brand name Tyrosilane (INCI name: Methylsilanol and Acetyl Tyrosine) by the company Exymol; peptides known for their effect in activating melanogenesis, for example the product sold under the brand name Bronzing SF Peptide powder (INCI name: Dextran and Octapeptide-5) by the company Infinitec Activos, the product sold under the brand name Melitane (INCI name: Glycerin and Aqua and Dextran and Acetyl Hexapeptide-1) comprising acetyl hexapeptide-1 known for its α-MSH agonist action, the product sold under the brand name Melatimes Solutions™ (INCI name: Butylene Glycol, Palmitoyl Tripeptide-40) by the company Lipotec, sugars and sugar derivatives, for example the product sold under the brand name Tanositol™ (INCI name: Inositol) by the company Provital, the product sold under the brand name Thalitan™ (or Phycosaccharide™ AG) by the company Codif International (INCI name: Aqua and Hydrolyzed algin (*Laminaria digitata*) and magnesium sulfate and manganese sulfate) containing an oligosaccharide of marine origin (guluronic acid and mannuronic acid chelated with magnesium and manganese ions), the product sold under the brand name Melactiva™ (INCI name: Maltodextrin, *Mucuna pruriens* Seed Extract) by the company Alban Muller, compounds rich in flavonoids, for example the product sold under the brand name Biotanning (INCI name: Hydrolyzed citrus Aurantium dulcin fruit extract) by the company Silab and known to be rich in lemon flavonoids (of the hesperidin type); agents intended for treating head hair and/or bodily hair, for example agents for protecting the melanocytes of the hair follicle, intended to protect said melanocytes against cytotoxic agents responsible for the senescence and/or apoptosis of said melanocytes, such as mimetics of DOPAchrome tautomerase activity, selected from those described in the European patent application published under the number EP 1 515 688 A2, the synthetic SOD mimetic molecules, for example manganese complexes, antioxidant compounds, for example cyclodextrin derivatives, siliceous compounds derived from ascorbic acid, lysine or arginine pyrrolidone carboxylate, combinations of mono- and diesters of cinnamic acid and of vitamin C, and more generally those mentioned in the European patent application published under the number EP 1 515 688 A2.

Examples of antioxidants that may be combined with said self-invertible inverse latex as defined previously in said compositions (F) and (G) include EDTA and its salts, citric acid, tartaric acid, oxalic acid, BHA (butylated hydroxyanisole), BHT (butylated hydroxytoluene), tocopherol derivatives, such as tocopheryl acetate, mixtures of antioxidant compounds, such as Dissolvine™ GL 47S sold by the company AkzoNobel under the INCI name: Tetrasodium Glutamate Diacetate.

Examples of sunscreens that may be combined with said self-invertible inverse latex as defined previously in said compositions (F) and (G) include all those appearing in the amended Cosmetics Directive 76/768/EEC, Annex VII.

Among the organic sunscreens that may be combined with said self-invertible inverse latex as defined previously in said compositions (F) and (G) are the family of benzoic acid derivatives, for instance para-aminobenzoic acids (PABA), notably monoglyceryl esters of PABA, ethyl esters of N,N25-propoxy PABA, ethyl esters of N,N-diethoxy PABA, ethyl esters of N,N-dimethyl PABA, methyl esters of N,N-dimethyl PABA and butyl esters of N,N-dimethyl PABA; the family of anthranilic acid derivatives, for instance homomenthyl-N-acetyl anthranilate; the family of salicylic acid derivatives, for instance amyl salicylate, homomenthyl salicylate, ethylhexyl salicylate, phenyl salicylate, benzyl salicylate and p-isopropanolphenyl salicylate; the family of cinnamic acid derivatives, for instance ethylhexyl cinnamate, ethyl-4-isopropyl cinnamate, methyl 2,5-diisopropylcinnamate, p-methoxypropyl cinnamate, p-methoxyisopropyl cinnamate, p-methoxyisoamyl cinnamate, p-methoxyoctyl cinnamate (p-methoxy 2-ethylhexyl cinnamate), p-methoxy-2-ethoxyethyl cinnamate, p-methoxycyclohexyl cinnamate, ethyl-α-cyano-β-phenyl cinnamate, 2-ethylhexyl-α-cyano-β-phenyl cinnamate or glyceryl di-para-methoxymono-2-ethylhexanoyl cinnamate; the family of benzophenone derivatives, for instance 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl 4'-phenylbenzophenone-2-5-carboxylate, 2-hydroxy-4-n-octyloxybenzophenone, 4-hydroxy-3-carboxybenzophenone; 3-(4'-methylbenzylidene)-d,l-camphor, 3-(benzylidene)-d,l-camphor, camphor benzalkonium methosulfate; urocanic acid, ethyl urocanate; the family of sulfonic acid derivatives, for instance 2-phenylbenzimidazole-5-sulfonic acid and salts thereof; the family of triazine derivatives, for instance hydroxyphenyltriazine, ethylhexyloxyhydroxyphenyl)-4-methoxyphenyltriazine, 2,4,6-trianillino(p-carbo-2'-ethylhexyl-1'-oxy)-1,3,5-triazine, 4,4-((6-(((1,1-dimethylethyl)amino)carbonyl)phenyl)amino)-1,3,5-triazine-2,4-diyldiimino)bis(2-ethylhexyl) benzoate, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methyphenyl)benzotriazole; dibenzazine; dianisoylmethane, 4-methoxy-4"-t-butylbenzoylmethane; 5-(3,3-dimethyl-2-norbornylidene)-3-pentan-2-one; the family of diphenylacrylate derivatives, for instance 2-ethylhexyl 2-cyano-3,3-diphenyl-2-propenoate, ethyl 2-cyano-3,3-diphenyl-2-propenoate; the family of polysiloxanes, for instance benzylidene siloxane malonate.

The mineral sunscreens, also known as "mineral sunblocks", that may be combined with said self-invertible inverse latex as defined previously in said compositions (F) and (G) include titanium oxides, zinc oxides, cerium oxide, zirconium oxide, yellow, red or black iron oxides, or chromium oxides. These mineral sunblocks may or may not be micronized, may or may not have been subjected to surface treatments and may optionally be presented in the form of aqueous or oily predispersions.

DESCRIPTION OF THE PREFERRED EMBODIMENTS

The invention will now be described in greater detail by means of the examples below.

EXAMPLES 1.1 Preparation of an inverse latex (IL1) comprising a crosslinked copolymer of the sodium salt of 2-methyl-[(1-oxo-2-propenyl)amino]-1-propanesulfonic acid and of acrylic acid partially salified in sodium salt form containing ethylenediaminedisuccinic acid in trisodium salt form as sequestering agent.

The following are placed in a beaker with stirring:

277 grams of deionized water, 73.1 grams of glacial acrylic acid, 308 grams of 2-methyl-[(1-oxo-2-propenyl)amino]-1-propanesulfonic acid, 141 grams of an aqueous 48 wt % solution of sodium hydroxide, 0.62 gram of a commercial 35 wt % solution of ethylenediaminedisuccinic acid in trisodium salt form (sold under the brand name Natriquest™ E30), 0.128 gram of methylenebis(acrylamide), 0.1 gram of copper sulfate pentahydrate (i.e. an amount of 160 molar ppm relative to the sum of the number of moles of 2-methyl-[(1-oxo-2-propenyl)amino]-1-propanesulfonic acid and of the number of moles of acrylic acid).

The pH of the aqueous phase is adjusted to 5.4 and the solution is made up with deionized water to 682 g.

The organic phase is prepared at the same time:

220 grams of isohexadecane 25 grams of Montane 80, 0.2 gram of azobis(isobutyronitrile) (AIBN).

The aqueous phase prepared above is gradually added to the oily phase and then dispersed using an Ultra-Turrax™ rotor-stator sold by the company IKA.

The emulsion obtained is then transferred to a jacketed reactor and sparged with nitrogen in order to remove the oxygen. A solution containing 0.42% by weight of cumene hydroperoxide in isohexadecane is introduced and the emulsion is kept stirring for 5 minutes of homogenization at room temperature.

An aqueous solution of 0.1% sodium metabisulfite in 25 g of water is introduced using a pump with a flow rate of 0.5 ml/minute in order to initiate the polymerization reaction.

The temperature of the medium will increase until a plateau is reached. The reaction medium is then heated at 85° C. for 1 h and then the whole medium is cooled to about 35° C., and 50 g of Polysorbate 80 sold under the brand name Montanox™ 80 are added.

The resulting self-invertible inverse latex is evaluated by observation of its appearance at 25° C., by its viscosity at 25° C., by the viscosity of an aqueous gel containing 2% by mass of a self-invertible inverse latex, by the viscosity of an aqueous gel at 3% by mass in the presence of 0.1% by mass of sodium chloride.

This test is referenced (IL1).

The results obtained are given in table 1 below.

1.2 Preparation of an inverse latex (IL2) comprising a crosslinked copolymer of the sodium salt of 2-methyl-[(1-oxo-2-propenyl)amino]-1-propanesulfonic acid and of partially salified acrylic acid containing sodium diethylenetriaminepentaacetate as sequestering agent. The same protocol as in the preceding example is performed using 0.45 g of a solution containing 40% by weight of sodium diethylenetriaminepentaacetate (sold under the brand name Versenex™ 80) instead of the solution of ethylenediaminedisuccinic acid in trisodium salt form.

This test is referenced (IL2).

1.3 Preparation of an inverse latex (IL3) comprising a crosslinked copolymer of the sodium salt of 2-methyl-[(1-oxo-2-propenyl)amino]-1-propanesulfonic acid and of partially salified acrylic acid containing N,N-diacetic glutamic acid tetrasodium salt (Dissolvine GLDA 47-S) as sequestering agent.

The same protocol as in example 1.1 is performed, using 2 g of a solution containing 47% by weight of N,N-diacetic glutamic acid tetrasodium salt (sold under the brand name DissolvineTMGLDA 47-S) instead of the solution of ethylenediaminedisuccinic acid in trisodium salt form.

This test is referenced (IL3).

1.4 Preparation of an inverse latex (IL4) comprising a crosslinked copolymer of the sodium salt of 2-methyl-[(1-oxo-2-propenyl)amino]-1-propanesulfonic acid and of partially salified acrylic acid.

The same protocol as in example 1.1 is performed, without using sequestering agent.

The test is referenced (IL4).

1.5 Preparation of an inverse latex (IL5) comprising a crosslinked copolymer of the sodium salt of 2-methyl-[(1-oxo-2-propenyl)amino]-1-propanesulfonic acid and of partially salified acrylic acid containing ethylenediaminedisuccinic acid in trisodium salt form as sequestering agent.

The same protocol as in example 1.1 is performed, while reducing the amount of sequestering agent to 0.15 g of ethylenediaminedisuccinic acid in trisodium salt form (sold under the brand name Natriquest™ E30).

The test is referenced (IL5).

1.6 Preparation of an inverse latex (IL6) comprising a crosslinked copolymer of the sodium salt of 2-methyl-[(1-oxo-2-propenyl)amino]-1-propanesulfonic acid and of partially salified acrylic acid containing ethylenediaminedisuccinic acid in trisodium salt form as sequestering agent and without addition of CuSO4.

The copolymer was prepared following the same protocol as example 1.1 but without adding copper sulfate, and thus without adding a Cu2+ salt.

The test is referenced (IL6).

TABLE 1

| | sequestering agent | Polymerization | | | Characterizations | | |
|---|---|---|---|---|---|---|---|
| Test No. | (amount in molar ppm) (*) | Inhibition (min) | Exothermicity (° C.) | Polymerization time (min) | Viscosity of latex at 25° C., mPa · s (Brookfield RVT, Spindle 3, Speed 20) | Viscosity of aqueous gel at 2% by mass, mPa · s (Brookfield RVT, Spindle 6, Speed 5) | Viscosity of aqueous gel at 3% by mass + 0.1% NaCl, mPa · s (Brookfield RVT, Spindle 6, Speed 5) |
| IL4 | / | 33 | No initiation of polymerization | | | | |
| (IL2) | Versenex ™ 80 (150 ppm) | 0 | 34 | 16 | 910 | 97000 | 6000 |
| (IL1) | Natriquest ™ E30 250 ppm | 0 | 34.3 | 15 | 1000 | 77000 | 6800 |
| (IL3) | Dissolvine ™ GLDA 47-S (1137 ppm) | 0 | 14.6 | 28 | nr | nr | nr |
| (IL5) | Natriquest ™ E30 (60 ppm) | | | No initiation of polymerization | | | |
| (IL6) | Natriquest ™ E30 (250 ppm) | 1 | 35.8 | 15 | 830 | 68000 | 4800 |

Properties of the copolymers obtained in examples 1.1, 1.2, 1.3, 1.4, 1.5 and 1.6.

(*): The amount of sequestrant is expressed in molar ppm and calculated relative to the molar sum of the two monomers (2-methyl-[(1-oxo-2-propenyl)amino]-1-propanesulfonic acid and acrylic acid).

Test (IL4) shows the impact of the proven presence of metal cations on the progression of the polymerization process: in the presence of copper cations (in this case at least 160 molar ppm of $Cu2+$ ions) and in the absence of any sequestering agent, the polymerization reaction does not take place. The introduction of the sodium diethylenetriaminepentaacetate (sold under the brand name Versenex™ 80) in test (IL2) allows the polymerization reaction to take place and leads to a polymer being obtained that has thickening properties in water and in saline solution.

In comparison, the use of ethylenediaminedisuccinic acid in trisodium salt form (sold under the brand name Natriquest™ E30) in test (IL1), under stoichiometric conditions identical to test (IL2), makes it possible to obtain polymerization kinetics similar to those observed for test (IL2) and a self-invertible inverse latex that has equivalent viscosifying performance. As test (IL5) shows, the amount of ethylenediaminedisuccinic acid in trisodium salt form must be high enough: introduced at a lower dose (60 molar ppm), it does not make it possible to complex all of the cations, which results in the absence of initiation of the polymerization. Furthermore, test (IL6), free of added copper cations, shows that the process takes place in an identical manner: ethylenediaminedisuccinic acid in trisodium salt form as is has no impact on the polymerization reaction.

Test (IL3) demonstrates the lower efficacy of N,N-diacetic glutamic acid tetrasodium salt (sold under the brand name DissolvineTMGLDA 47-S), despite its higher chelating capacity (85 milligrams of Cu/gram of sequestrant [1]) than that of ethylenediaminedisuccinic acid in trisodium salt form (18.4 milligrams of Cu/gram of sequestrant [2]). Specifically, added before the polymerization under identical stoichiometric conditions, N,N-diacetic glutamic acid tetrasodium salt enables initiation of the polymerization reaction but the kinetics are slower than in test (IL2) and than in test (IL1): the reaction time is almost twice as long. Similarly, the exothermicity observed is lower, which suggests that the conversion of the monomers is not complete. The process has therefore not taken place properly.

[1]: "Product Data Sheet" from the company Nouryon, Dissolvine GL-47-S of Jul. 3, 2019

[2]: Technical sheet for Natriquest, from the company Ineos, "Issue March 2008".

[3]: "technical data sheet; Versenex™80", from the company Dow, "Form No. 113-01342-0812 AMS", published in August 2012.

II: Illustrative Cosmetic Formulations

In the formulations below, the percentages are expressed as mass percentages per 100% of the mass of the formulation.

Example II-1: Care Cream

Cyclomethicone: 10%
Self-invertible inverse latex (IL6): 0.8%
Montanov™ 68: 2%
Stearyl alcohol: 1%
Stearic alcohol: 0.5%
Preserving agent: 0.65%
Lysine: 0.025%
Xanthan gum: 0.2%
Glycerol: 3%
Water: qs 100%

Example II-2: Antisun Milk

Formula
A Montanov™ 68: 3.0%
Sesame oil: 5.0%
Parsol™ MCX: 5.0%
λ-Carrageenan: 0.10%
B Water: qs 100%
C Self-invertible inverse latex (IL6): 0.80%
D Fragrance: qs
Preserving agent: qs Procedure
Emulsify B in A at 60° C., then add C at approximately 60° C., then D at approximately 30° C. and adjust the pH, if necessary.

Example II-3: Body Milk

Montanov™ 202: 3.5%
Lanol™ 37T: 8.0%
Solagum™ L: 0.05%
Water: qs 100%
Benzophenone-3: 2.0%
Dimethicone 350 cPs: 0.05%
Self-invertible inverse latex (IL6): 2.5%
Preserving agent: 0.2%
Fragrance: 0.4%

Example II-4: Makeup-Removing Emulsion Comprising Sweet Almond Oil

Montanov™ 202: 5%
Sweet almond oil: 5%
Water: qs 100%
Self-invertible inverse latex (IL6): 0.3%
Glycerol: 5%
Preserving agent: 0.2%
Fragrance: 0.3%

Example II-5: Moisturizing Cream for Greasy Skin

Montanov™ 68: 5%
Cetylstearyl octanoate: 8%
Octyl palmitate: 2%
Water: qs 100%
Self-invertible inverse latex (IL6): 2.6%
Micropearl™ M100: 3.0%
Mucopolysaccharides: 5%
Sepicide™ HB: 0.8%
Fragrance: 0.3%

Example II-6: Makeup-Removing Milk

Montanov™ 68: 3%
Primol™ 352: 8.0%
Sweet almond oil: 2%
Water: qs 100%
Self-invertible inverse latex (IL6): 0.8%
Preserving agent: 0.2%

Example II-7: Antisun Milk

Montanov™ L: 3.5%
Lanol™ 37T: 10.0%
Parsol™ MCX: 5.0%
Eusolex™ 4360: 2.0%
Water: qs 100%
Self-invertible inverse latex (IL6): 1.8%
Preserving agent: 0.2%
Fragrance: 0.4%

Example II-8: Sunless Tanning Emulsion

Lanol™ 99: 15%
Montanov™ 68: 3.0%
Parsol™ MCX: 3.0%
Water: qs 100%
Dihydroxyacetone: 5.0%
Monosodium phosphate: 0.2%
Self-invertible inverse latex (IL6): 2.5%
Fragrance: 0.3%
Sepicide™ HB: 0.8%
Sodium hydroxide: qs pH=5

Example II-9: Care Cream

Cyclomethicone: 10%
Self-invertible inverse latex (IL6): 2.8%
Montanov™ 202: 4.5%
Preserving agent: 0.65%
Lysine: 0.025%
Xanthan gum: 0.2%
Glycerol: 3%
Water: qs 100%

Example II-10: Antisun Cream

Simulsol™ 165: 3%
Montanov™ 68: 2%
C12-C15 benzoate: 8%
Pecosil™ PS 100: 2%
Dimethicone: 2%
Cyclomethicone: 5%
Octyl para-methoxycinnamate: 6%
Benzophenone-3: 4%
Titanium oxide: 8%
Xanthan gum: 0.2%
Butylene glycol: 5%
Demineralized water: qs 100%
Self-invertible inverse latex (IL6): 1.5%
Preserving agent, fragrance: qs Example II-11: Antisun and Self-Tanning Gel Montanov™ 68: 3.0%
Glyceryl triheptanoate: 10.0%
Deepaline™ PVB: 1.05%
Self-invertible inverse latex (IL6): 2.2%
Water: qs 100%
Dihydroxyacetone: 5%
Fragrance: 0.1%
Sepicide™ HB: 0.3%
30 Sepicide™ CI: 0.1%
Parsol™ MCX: 4.0%

The invention claimed is:

1. A self-invertible inverse latex comprising an aqueous phase comprising:
- a) a crosslinked anionic polyelectrolyte (P) consisting of:
  - at least one first monomer unit resulting from 2-methyl-2-[(1-oxo-2-propenyl)amino]-1-propanesulfonic acid in free acid form or partially or totally salified form; and
  - at least one second monomer unit derived from at least one monomer chosen from the elements of the group consisting of acrylic acid, methacrylic acid, 2-carboxyethylacrylic acid, itaconic acid, maleic acid, 3-methyl-3-[(1-oxo-2-propenyl)amino]butanoic acid, the carboxylic function of said monomers being in free acid form or partially salified or totally salified form; and
  - at least one third monomer unit derived from a polyethylenic crosslinking monomer (AR), and
- b) ethylenediaminedisuccinic acid in trisodium salt form, in an amount of at least 250 molar ppm calculated relative to the molar sum of said first and second monomer units.

2. The inverse latex as claimed in claim 1, wherein the polyethylenic crosslinking monomer (AR) is chosen from methylenebis(acrylamide), ethylene glycol dimethacrylate, diethylene glycol diacrylate, ethylene glycol diacrylate, diallylurea, triallylamine, trimethylolpropane triacrylate, diallyloxyacetic acid or a salt thereof, or a mixture of these compounds.

3. The inverse latex as claimed in claim 1, wherein the crosslinking monomer (AR) is methylenebis(acrylamide) or triallylamine.

4. The inverse latex as claimed in claim 1, wherein the crosslinked anionic polyelectrolyte comprises, per 100 mol %:
- a proportion of between 20 mol % and 90 mol % of the monomer unit derived from 2-methyl-2-[(1-oxo-2-propenyl)amino]-1-propanesulfonic acid in free acid form or partially or totally salified form;
- a proportion of between 10 mol % and 80 mol % of the monomer unit derived from at least one monomer chosen from the elements of the group consisting of acrylic acid, methacrylic acid, 2-carboxyethylacrylic acid, itaconic acid, maleic acid, 3-methyl-3-[(1-oxo-2-propenyl)amino] butanoic acid, the carboxylic function of said monomers being in free acid form or partially salified or totally salified form; and
- a proportion of greater than 0 mol % and less than or equal to 1 mol % of monomer units derived from at least one polyethylenic crosslinking monomer (AR).

5. A process for preparing an inverse latex as defined in claim 1, comprising the following steps:
- a) preparing the aqueous phase,
- b) preparing an organic phase comprising at least one oil (O) and an emulsifying system (S1) of water-in-oil type,
- c) mixing the aqueous phase and the organic phase prepared in steps a) and b) and emulsifying so as to form an emulsion,
- d) inertizing the emulsion with nitrogen,
- e) initiating the polymerization reaction by introduction, into the inertized emulsion, of a free-radical initiator, and
- f) introduction, into the reaction medium resulting from step e), of an emulsifying system (S2) of oil-in-water type at a temperature of between 30° C. and 60° C.

6. The process as claimed in claim 5, further comprising between steps a) and b) a step of adding, to the aqueous phase prepared in step a), a solution chosen from a sodium hydroxide solution, a potassium hydroxide solution, an ammonium hydroxide solution, a monoethanolamine salt solution and a lysine salt solution.

7. The process as claimed in claim 5, wherein, in step e), the radical initiator is a redox pair which generates hydrogen sulfite ($HSO_3^-$) ions.

8. The process as claimed in claim 5, wherein, in step e), a polymerization coinitiator is introduced into the inertized emulsion.

9. The process as claimed in claim 5, wherein, in step a), the pH of the aqueous phase is adjusted to between 3.0 and 7.0.

10. The process as claimed in claim 5, wherein the reaction medium derived from step e) is concentrated by distillation before performing step f).

11. The process as claimed in claim 5, wherein the reaction medium derived from step e) or f) is spray-dried.

12. A thickening and/or emulsifying and/or stabilizing agent for a topical cosmetic composition, comprising the inverse latex of claim 1.

13. A topical cosmetic composition (F), comprising as thickener, per 100% of its total mass, between 0.1% and 10% by mass of said inverse latex as defined in claim 1.

14. A topical pharmaceutical composition (G), comprising, as thickener, per 100% of its total mass, between 0.1% and 10% by mass of said inverse latex as defined in claim 1.

15. The process of claim 7, wherein the redox pair is the cumene hydroperoxide/sodium metabisulfite ($Na_2S_2O_5$) pair.

16. The process of claim 7, wherein the redox pair is the cumene hydroperoxide/thionyl chloride ($SOCl_2$) pair.

17. The process of claim 8, wherein the polymerization coinitiator is azobis(isobutyronitrile).

18. The inverse latex as claimed in claim 1, wherein the polyethylenic crosslinking monomer (AR) is chosen from methylenebis(acrylamide), ethylene glycol dimethacrylate, diethylene glycol diacrylate, ethylene glycol diacrylate, diallylurea, triallylamine, trimethylolpropane triacrylate, diallyloxyacetic acid or a salt thereof, or a mixture of these compounds.

19. The inverse latex as claimed in claim 2, wherein the polyethylenic crosslinking monomer (AR) is chosen from methylenebis(acrylamide), ethylene glycol dimethacrylate, diethylene glycol diacrylate, ethylene glycol diacrylate, diallylurea, triallylamine, trimethylolpropane triacrylate, diallyloxyacetic acid or a salt thereof, or a mixture of these compounds.

* * * * *